US008927004B1

(12) United States Patent
Dehnad et al.

(10) Patent No.: US 8,927,004 B1
(45) Date of Patent: Jan. 6, 2015

(54) BIOABSORBABLE SUBSTRATES AND SYSTEMS THAT CONTROLLABLY RELEASE ANTIMICROBIAL METAL IONS

(71) Applicant: Silver Bullet Therapeutics, Inc., San Jose, CA (US)

(72) Inventors: Houdin Dehnad, El Granada, CA (US); Paul E. Chirico, Campbell, CA (US); Bohdan Wolodymyr Chopko, Henderson, NV (US); John Barr, San Diego, CA (US); Robert Vincent McCormick, Saratoga, CA (US); Julie Lucero, San Jose, CA (US); Jason A. Jegge, San Jose, CA (US)

(73) Assignee: Silver Bullet Therapeutics, Inc., San Jose, CA (US)

( * ) Notice: Subject to any disclaimer, the term of this patent is extended or adjusted under 35 U.S.C. 154(b) by 0 days.

(21) Appl. No.: 14/302,352

(22) Filed: Jun. 11, 2014

(51) Int. Cl.
*A61K 33/34* (2006.01)
*A61K 33/30* (2006.01)
*A61K 33/38* (2006.01)
*A61L 31/02* (2006.01)
*A61L 31/08* (2006.01)

(52) U.S. Cl.
CPC ............... *A61L 31/022* (2013.01); *A61L 31/08* (2013.01)
USPC ........... 424/423; 424/400; 424/618; 424/630; 424/641

(58) Field of Classification Search
CPC ....... A61K 33/30; A61K 33/34; A61K 33/38; A61K 8/27; A61L 31/16; A61L 2300/404; A61L 27/54; A01N 59/16; A01N 59/20
USPC .......................... 424/423, 400, 618, 630, 641
See application file for complete search history.

(56) References Cited

U.S. PATENT DOCUMENTS

| 3,921,632 | A | 11/1975 | Bardani |
| 4,292,968 | A | 10/1981 | Ellis |
| 4,314,554 | A | 2/1982 | Greatbatch |
| 4,405,311 | A | 9/1983 | Greatbatch |
| 4,615,705 | A | 10/1986 | Scales et al. |
| 4,772,266 | A | 9/1988 | Groshong |
| 4,849,223 | A | 7/1989 | Pratt et al. |
| 5,290,271 | A | 3/1994 | Jernberg |
| 5,372,599 | A | 12/1994 | Martins |
| 5,423,859 | A | 6/1995 | Koyfman et al. |
| 5,454,886 | A | 10/1995 | Burrell et al. |
| 5,549,603 | A | 8/1996 | Feiring |
| 5,681,575 | A | 10/1997 | Burrell et al. |
| 5,695,857 | A | 12/1997 | Burrell et al. |
| 5,770,255 | A | 6/1998 | Burrell et al. |
| 5,788,687 | A | 8/1998 | Batich et al. |
| 5,958,440 | A | 9/1999 | Burrell et al. |
| 5,985,308 | A | 11/1999 | Burrell et al. |
| 6,080,490 | A | 6/2000 | Burrell et al. |
| 6,117,296 | A | 9/2000 | Thomson |
| 6,287,484 | B1 | 9/2001 | Hausslein et al. |
| 6,312,469 | B1 | 11/2001 | Gielen et al. |
| 6,451,003 | B1 | 9/2002 | Prosl et al. |
| 6,458,092 | B1 | 10/2002 | Gambale et al. |
| 6,458,889 | B1 | 10/2002 | Trollsas et al. |
| 6,478,790 | B2 | 11/2002 | Bardani |
| 6,500,165 | B1 | 12/2002 | Frank |
| 6,522,918 | B1 | 2/2003 | Crisp et al. |
| 6,558,388 | B1 | 5/2003 | Bartsch et al. |
| 6,613,807 | B2 | 9/2003 | Uhrich |
| 6,616,678 | B2 | 9/2003 | Nishtala et al. |
| 6,716,895 | B1 | 4/2004 | Terry |
| 6,719,987 | B2 | 4/2004 | Burrell et al. |
| 6,773,429 | B2 | 8/2004 | Sheppard, Jr. et al. |
| 6,830,747 | B2 | 12/2004 | Lang et al. |
| 6,840,919 | B1 | 1/2005 | Håkansson |
| 6,913,763 | B2 | 7/2005 | Lerner |
| 6,936,006 | B2 | 8/2005 | Sabra |
| 6,936,270 | B2 | 8/2005 | Watson et al. |
| 6,960,215 | B2 | 11/2005 | Olson, Jr. et al. |
| 7,147,865 | B2 | 12/2006 | Fishman et al. |
| 7,179,849 | B2 | 2/2007 | Terry |
| 7,223,227 | B2 | 5/2007 | Pflueger |

(Continued)

FOREIGN PATENT DOCUMENTS

| WO | WO 99/44538 A1 | 9/1999 |
| WO | WO 00/47273 A1 | 8/2000 |
| WO | WO 02/009767 A2 | 2/2002 |
| WO | WO 03/049798 A2 | 6/2003 |
| WO | WO 2004/006885 A2 | 1/2004 |
| WO | WO 2004/026357 A1 | 4/2004 |

(Continued)

OTHER PUBLICATIONS

Dehnad et al.; U.S. Appl. No. 13/748,546 entitled "Bone Implant and Systems That Controllably Releases Silver," filed Jan. 23, 2013.
Dehnad et al.; U.S. Appl. No. 13/527,389 entitled "Bone implants for the treatment of infection," filed Jun. 19, 2012.

*Primary Examiner* — Frederick Krass
*Assistant Examiner* — Tracy Liu
(74) *Attorney, Agent, or Firm* — Shay Glenn LLP

(57) ABSTRACT

Bioabsorbable substrates having antimicrobial metal ion coatings that are well suited for implantation in to a subject's body to treat and/or prevent infection. In particular, described herein are flexible bioabsorbable filaments that are coated with an anodic metal (e.g., silver and/or zinc and/or copper) that is co-deposited with a cathodic metal (e.g., palladium, platinum, gold, molybdenum, titanium, iridium, osmium, niobium or rhenium) on the filament so that the anodic metal is galvanically released as antimicrobial ions when the apparatus is inserted into a subject's body. The anodic metal may be at least about 30 percent by volume of the coating.

26 Claims, 9 Drawing Sheets

(56) References Cited

U.S. PATENT DOCUMENTS

| | | |
|---|---|---|
| 7,255,713 B2 | 8/2007 | Malek |
| 7,456,012 B2 | 11/2008 | Ryttén et al. |
| 7,457,667 B2 | 11/2008 | Skiba |
| 7,632,277 B2 | 12/2009 | Woll et al. |
| 7,662,176 B2 | 2/2010 | Skiba et al. |
| 7,672,719 B2 | 3/2010 | Skiba et al. |
| 7,704,520 B1 | 4/2010 | Calhoun |
| 7,727,221 B2 | 6/2010 | Penner et al. |
| 7,824,699 B2 | 11/2010 | Ralph et al. |
| 7,846,162 B2 | 12/2010 | Nelson |
| 7,904,147 B2 | 3/2011 | Schneider et al. |
| 7,919,111 B2 | 4/2011 | Chudzik et al. |
| 7,951,853 B2 | 5/2011 | Ismail et al. |
| 7,955,636 B2 | 6/2011 | Terry |
| 7,985,415 B2 | 7/2011 | Giroux |
| 8,048,150 B2 | 11/2011 | Weber et al. |
| 8,052,743 B2 | 11/2011 | Weber et al. |
| 8,080,055 B2 | 12/2011 | Atanasoska et al. |
| 8,114,148 B2 | 2/2012 | Atanasoska et al. |
| 8,118,857 B2 | 2/2012 | VanCamp et al. |
| 8,178,120 B2 * | 5/2012 | Vandesteeg et al. .......... 424/411 |
| 8,221,396 B2 | 7/2012 | Dehnad et al. |
| 8,236,046 B2 | 8/2012 | Weber |
| 8,267,992 B2 | 9/2012 | Atanasoska et al. |
| 8,309,216 B2 | 11/2012 | Ohrlander et al. |
| 8,591,531 B2 | 11/2013 | Buevich et al. |
| 8,636,753 B2 | 1/2014 | Buevich et al. |
| 8,771,323 B2 | 7/2014 | Dehnad et al. |
| 2002/0029043 A1 | 3/2002 | Ahrens et al. |
| 2002/0031601 A1 | 3/2002 | Darouiche et al. |
| 2002/0082679 A1 | 6/2002 | Sirhan et al. |
| 2002/0111603 A1 | 8/2002 | Cheikh |
| 2002/0143302 A1 | 10/2002 | Hinchliffe et al. |
| 2003/0050689 A1 | 3/2003 | Matson |
| 2004/0039441 A1 | 2/2004 | Rowland et al. |
| 2004/0223944 A1 | 11/2004 | Capelli |
| 2004/0267234 A1 | 12/2004 | Heart et al. |
| 2005/0004558 A1 | 1/2005 | Gambale et al. |
| 2005/0125054 A1 | 6/2005 | Bhat et al. |
| 2005/0152949 A1 | 7/2005 | Hotchkiss et al. |
| 2005/0177103 A1 | 8/2005 | Hunter et al. |
| 2005/0181004 A1 | 8/2005 | Hunter et al. |
| 2005/0256525 A1 | 11/2005 | Culbert et al. |
| 2005/0271701 A1 | 12/2005 | Cottone et al. |
| 2006/0004431 A1 | 1/2006 | Fuller et al. |
| 2006/0030872 A1 | 2/2006 | Culbert et al. |
| 2006/0041182 A1 | 2/2006 | Forbes et al. |
| 2006/0264698 A1 * | 11/2006 | Kondonis et al. ............... 600/37 |
| 2007/0016163 A1 | 1/2007 | Santini, Jr. et al. |
| 2007/0141106 A1 | 6/2007 | Bonutti et al. |
| 2007/0179609 A1 | 8/2007 | Goble et al. |
| 2007/0244548 A1 | 10/2007 | Myers et al. |
| 2007/0260054 A1 | 11/2007 | Chudzik |
| 2007/0298377 A1 | 12/2007 | Kenealy et al. |
| 2008/0009888 A1 | 1/2008 | Ewers et al. |
| 2008/0058733 A1 | 3/2008 | Vogt et al. |
| 2008/0109034 A1 | 5/2008 | Mather et al. |
| 2008/0147186 A1 | 6/2008 | Joshi et al. |
| 2008/0195033 A1 | 8/2008 | Eagleson et al. |
| 2008/0195223 A1 | 8/2008 | Eddin et al. |
| 2008/0319424 A1 | 12/2008 | Muni et al. |
| 2009/0004239 A1 | 1/2009 | Ladet et al. |
| 2009/0005867 A1 | 1/2009 | Lefranc et al. |
| 2009/0005869 A1 | 1/2009 | Laurencin et al. |
| 2009/0012350 A1 | 1/2009 | Tihon |
| 2009/0035342 A1 | 2/2009 | Karandikar et al. |
| 2009/0036744 A1 | 2/2009 | Vayser |
| 2009/0099613 A1 | 4/2009 | Vilims |
| 2009/0112236 A1 | 4/2009 | Stopek |
| 2009/0204129 A1 | 8/2009 | Fronio |
| 2009/0248048 A1 | 10/2009 | Milbocker |
| 2010/0076463 A1 | 3/2010 | Mavani et al. |
| 2010/0092531 A1 | 4/2010 | Odermatt et al. |
| 2010/0131051 A1 | 5/2010 | Peterson |
| 2010/0217370 A1 | 8/2010 | Scheuermann et al. |
| 2010/0249783 A1 | 9/2010 | Triue |
| 2010/0292756 A1 | 11/2010 | Schneider |
| 2010/0331966 A1 | 12/2010 | Borck |
| 2011/0091515 A1 | 4/2011 | Zilberman et al. |
| 2011/0125287 A1 | 5/2011 | Hotter et al. |
| 2011/0130774 A1 | 6/2011 | Criscuolo et al. |
| 2011/0153027 A1 | 6/2011 | Behan |
| 2011/0200655 A1 | 8/2011 | Black et al. |
| 2011/0257666 A1 | 10/2011 | Ladet et al. |
| 2012/0089232 A1 * | 4/2012 | Choi et al. .................. 623/18.11 |
| 2012/0123485 A1 * | 5/2012 | Dehnad et al. ................. 606/304 |
| 2012/0148633 A1 * | 6/2012 | Sun et al. ...................... 424/400 |
| 2013/0005829 A1 | 1/2013 | Jamiolkowski et al. |
| 2013/0018448 A1 | 1/2013 | Folan et al. |
| 2013/0045266 A1 | 2/2013 | Choi et al. |
| 2013/0158571 A1 | 6/2013 | Meneghin et al. |
| 2013/0164346 A1 | 6/2013 | Lee et al. |
| 2013/0172915 A1 | 7/2013 | Thomas et al. |
| 2013/0224276 A1 | 8/2013 | Hunter et al. |
| 2013/0245783 A1 | 9/2013 | Thull |
| 2013/0295184 A1 | 11/2013 | Choi et al. |

FOREIGN PATENT DOCUMENTS

| | | |
|---|---|---|
| WO | WO 2004/045549 A2 | 6/2004 |
| WO | WO 2005/049105 A2 | 6/2005 |
| WO | WO 2005/051448 A1 | 6/2005 |
| WO | WO 2006/135479 A2 | 12/2006 |
| WO | WO 2007/076376 A2 | 7/2007 |
| WO | WO 2007/109069 A2 | 9/2007 |
| WO | WO 2007/117214 A1 | 10/2007 |
| WO | WO 2011/031789 A1 | 3/2011 |
| WO | WO 2011/127149 A1 | 10/2011 |
| WO | WO 2013/004727 A1 | 1/2013 |
| WO | WO 2013/049106 A2 | 4/2013 |
| WO | WO 2013/049799 A1 | 4/2013 |
| WO | WO 2013/114145 A1 | 8/2013 |

* cited by examiner

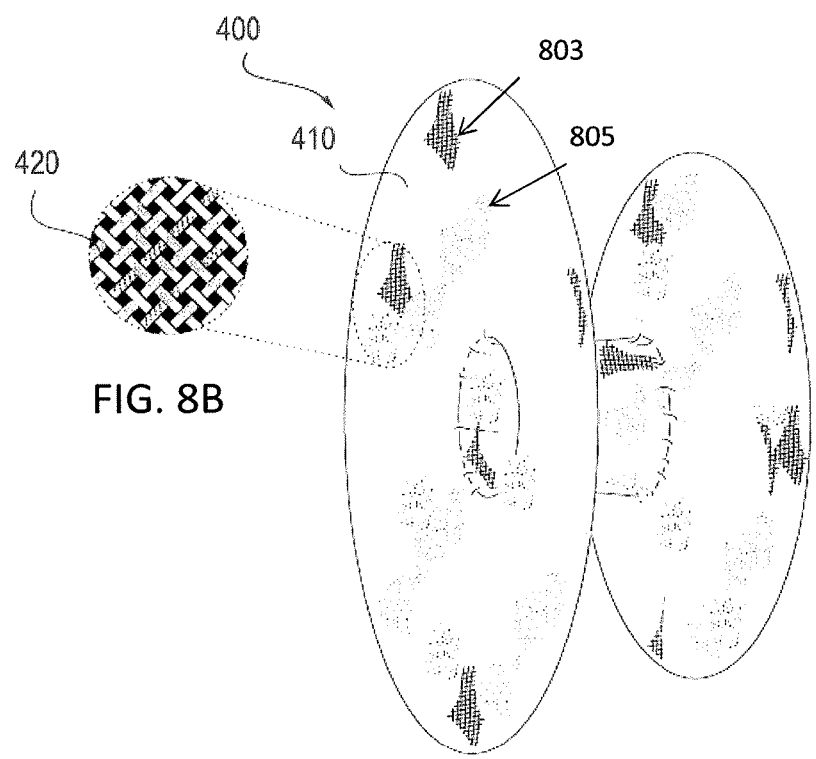
FIG. 8B
FIG. 8A
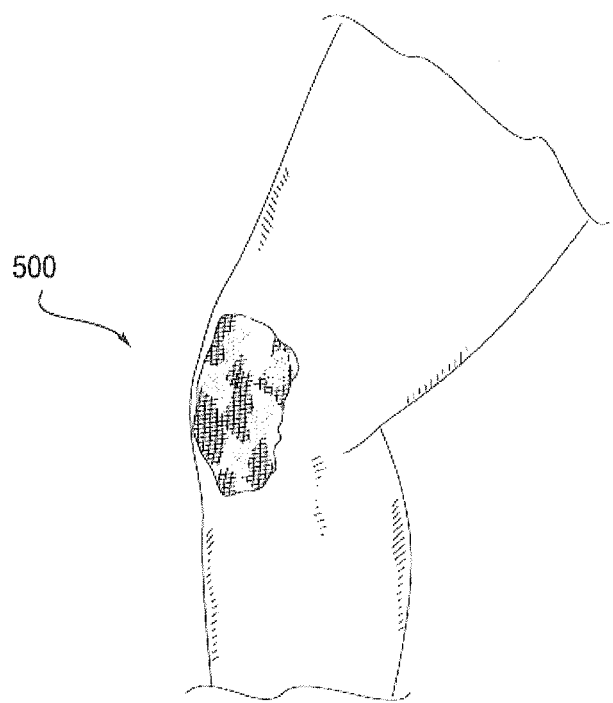
FIG. 9

BIOABSORBABLE SUBSTRATES AND SYSTEMS THAT CONTROLLABLY RELEASE ANTIMICROBIAL METAL IONS

CROSS REFERENCE TO RELATED APPLICATIONS

None.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are bioabsorbable substrates having antimicrobial metal ion coatings that are well suited for implantation in to a subject's body to treat and/or prevent infection. In particular, described herein are flexible bioabsorbable filaments that are coated with an anodic metal (e.g., silver and/or zinc and/or copper) that is co-deposited with a cathodic metal (e.g., palladium, platinum, gold, molybdenum, titanium, iridium, osmium, niobium or rhenium) on the filament so that the anodic metal is galvanically released as antimicrobial ions when the apparatus is inserted into a subject's body.

BACKGROUND

Antimicrobial or antibiotic agents are widely used to treat as well as to prevent infection. In particular, silver is known to be antimicrobial and has been used (primarily as a coating) in various medical devices with limited success. Both active (e.g., by application of electrical current) and passive (e.g., galvanic) release of silver ions have been proposed for use in the treatment and prevention of infection. However, the use of silver-releasing implants have been limited because of the difficulty in controlling and distributing the release of silver ions as well as the difficulty in maintaining a therapeutically relevant concentration of silver ions in an appropriate body region. Zinc shares many of the same antimicrobial properties of silver, but has been less commonly used, and thus even less is known about how to control the amount and distribution of the release of silver ions to treat and/or prevent infection.

It would be highly beneficial to use an antimicrobial agent such as silver and/or zinc as part of a bioabsorbable implant, in part because the risk of acquiring infections from bioabsorbable materials in medical devices is very high. Many medical applications exist for bioabsorbable materials including: wound closure (e.g., sutures, staples, adhesives), tissue repair (e.g., meshes, such as for hernia repair), prosthetic devices (e.g., internal bone fixation devices, etc.), tissue engineering (e.g., engineered blood vessels, skin, bone, cartilage, liver, etc.) and controlled drug delivery systems (such as microcapsules and ion-exchange resins). The use of bioabsorbable materials in medical applications such as these may reduce tissue or cellular irritation and the induction of an inflammatory response.

Bioabsorbable materials for medical applications are well known. For example, synthetic bioabsorbable polymers may include polyesters/polylactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers, as well as naturally derived polymers such as albumin, fibrin, collagen, elastin, chitosan, alginates, hyaluronic acid; and biosynthetic polyesters (e.g., 3-hydroxybutyrate polymers). However, like other biomaterials, bioabsorbable materials are also subjected to bacterial contamination and can be a source of infections which are difficult to control. Those infections quite often require their removal and costly antimicrobial treatments.

Efforts to render bioabsorbable materials more infection resistant generally have focused on impregnating the materials with antibiotics or salts such as silver salts, and have provided only limited, and instantaneous antimicrobial activity. It is desirable to have an antimicrobial effect which is sustained over time, such that the antimicrobial effect can be prolonged for the time that the bioabsorbable material is in place. This can range from hours or days, to weeks or even years.

Further, although antimicrobial/antibacterial metal coatings on medical devices have been suggested, metal coatings (such as silver or copper coatings) have not been characterized or optimized. In such applications, it is important that the metal coatings do not shed or leave behind large metal particulates in the body, which may induce unwanted immune responses and/or toxic effects. Further, it is essential that the release of the antimicrobial agent (metal) be metered over the lifetime of the implant.

For example, U.S. Pat. No. 8,309,216 describes substrates including degradable polymers that include an electron donor layer (such as silver, copper or zinc) onto which particles of palladium and platinum, plus one other secondary metal (chosen from gold, ruthenium, rhodium, osmium, iridium, or platinum) are deposited onto. Although such materials are described for anti-microbial implants (e.g., pacemakers, etc.), the separate layers formed by this method would be problematic for antimicrobial coatings in which the undercoating of silver, copper or zinc were being released, potentially undermining the platinum and secondary metal.

Similarly, U.S. Pat. No. 6,719,987 describes bioabsorbable materials having an antimicrobial metal (e.g., silver) coating that can be used for an implant. The silver coating is for release of particles (including ions) and must be in a crystalline form characterized by sufficient atomic disorder. In this example, the silver is also deposited in one or more layers. U.S. Pat. No. 6,080,490 also describes medical devices with antimicrobial surfaces that are formed by layers of metals (e.g., silver and platinum) to release ions; layers are etched to expose regions for release. The outer layer is always Palladium (and one other metal), beneath which is the silver.

Thus, it would be highly desirable to provide devices, systems and methods for the controlled release (particularly the controlled galvanic release) of a high level of silver, zinc or silver and zinc ions from a bioabsorbable material into the tissue for a sufficient period of time to treat or prevent infection.

Specifically, known systems and devices, including those described above, that have attempted to use ions (e.g., silver and/or zinc) on bioabsorbable materials to treat infection have suffered from problems such as: insufficient amounts of ions released (e.g., ion concentration was too low to be effective); insufficient time for treatment (e.g., the levels of ions in the body or body region were not sustained for a long enough period of time); and insufficient region or volume of tissue in which the ion concentration was elevated (e.g., the therapeutic region was too small or limited, such as just on the surface of a device). Further, the use of galvanic release has generally been avoided or limited because it may effectively corrode the metals involved, and such corrosion is generally considered an undesirable process, particularly in a medical device.

There is a need for antimicrobial coatings for bioabsorbable materials, which can create an effective and sustainable antimicrobial effect, which do not interfere with the bioabsorption of the bioabsorbable material, and which do not shed or leave behind large metal particulates in the body as the bioabsorbable material disappears.

Therapeutically, the level of silver and/or zinc ions released into a body is important, because it may determine how effective the antimicrobial ions are for treating or preventing infection. As described in greater detail below, the amount or ions released galvanically may depend on a number of factors which have not previously been well controlled. For example, galvanic release may be related to the ratio of the anode to the cathode (and thus, the driving force) as well as the level of oxygen available; given the galvanic reaction, the level of oxygen may be particularly important for at the cathode. Insufficient oxygen at the cathode may be rate-limiting for galvanic release.

For example, with respect to silver, it has been reported that a concentration of 1 mg/liter of silver ions can kill common bacteria in a solution. Silver ions may be generated a galvanic system with silver as the anode and platinum or other noble metal as the cathode. However one of the challenges in designing a galvanic system for creation of silver ion in the body that has not been adequately addressed is the appropriate ratios of the areas of the electrodes (e.g., anode to cathode areas) in order to create the germicidal level of free silver ions. One challenge in designing a galvanic system is addressing the parasitic loss of current due to formation of silver chloride via reaction:

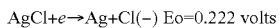

AgCl+$e$→Ag+Cl(−) Eo=0.222 volts

We herein propose that it may be beneficial to have an area of the cathode under common biological condition that is at least larger than 8% of the silver area to sustain the germicidal level of silver ions. For the purpose of this discussion, the following assumptions have been made: for a concentration of: $[H+]=10^{-7}$ moles/liter; $[OH-]=10^{-7}$ moles/liter; $[O2]=5*10^{-3}$ moles/liter in the capillary; $[Cl-]=0.1$ moles/liter. The values of the following were also assumed (as constants or reasonable approximations): Faraday's constant, F=96000 coulombs/mole; diffusivity of oxygen=0.000234 cm2/sec; diffusivity of Ag+=$10^{-6}$ cm2/sec; diffusivity of Cl−=$10^{-6}$ cm2/sec; R, Gas constant=8.314 J K$^{-1}$ mol-1; T, temp. K; Mw of silver=108 grams/mol; germicidal concentration of silver=$10^{-5}$ mol/liter.

At equilibrium, for a galvanic cell it is acceptable to assume that the two electrodes are at the same potential. Using the Nernst equation, the equilibrium concentration of oxygen when the silver ion is at the germicidal level may be calculated:

E=Eo−(RT/nF)ln [(Activity of products)/(activity of reactants)]

E=Eo−(0.0592/n)Log [(product)/(reactant)]

For the half cell reaction at the anode (silver electrode): Ag→Ag(+)+e(−). This reaction is written as a reduction reaction below:

Ag(+)+$e$(−)→Ag Eo=0.800 volt        eq. (1)

[Ag+]=1 mg/liter*(gr/1000 mg)*(1 mol/108 (Mw of Ag))=$10^{-5}$ Ag+mole/liter; E=0.800−(0.0592/1) log [1/($10^{-5}$)]. Based on this, the resulting E=8.00−(0.0592*5)=0.504 volt.

For the cathode, the reactions are:

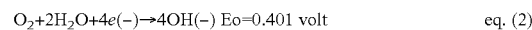

O$_2$+2H$_2$O+4$e$(−)→4OH(−) Eo=0.401 volt        eq. (2)

O$_2$+4H(+)+4$e$(−)→2H$_2$O Eo=1.229 volt        eq. (3)

In dilute aqueous solutions these two reactions are equivalent. At equilibrium the potential for the two half-cell potentials must be equal:

E=0.401−(0.0592/4)log {[OH(−)]^4/[O2]}

E(silver)=0.504=0.401−(0.0592/4)log {[$10^{-7}$]^4/[O2]}

Solving for [O$_2$], the result is: [O$_2$]=$10^{-21}$ atm. The result of this analysis is that, thermodynamically speaking, as long as the concentration of oxygen is above $10^{-21}$, the concentration of the sliver ion could remain at the presumed germicidal level.

However, a parasitic reaction to creation of silver ions is the formation of AgCl due to reaction of Cl− at the silver electrode. The half-cell potential for this reaction is:

AgCl+$e$(−)→Ag+Cl(−) Eo=0.222

Solving the Nernst equation for this reaction with E=0.504, the concentration of chloride $[Cl-]=2×10^{-5}$. The importance of this reaction becomes apparent in evaluating the current needed to compensate for the losses of current due to this reaction and the increased in ratio of the area of the cathode to the anode.

The current density per untul area requirements of the device can be estimated by combining Fick's and Faraday equations: the silver losses due to diffusion of silver from the device can be calculated using the Fick's equation:

$j=D[C(d)-C(c)]/d$        Fick's equation

The current needed to create the silver ions (A/cm2): i=j*n*F, where, j is the mass flux, C(d) is the concentration of the silver at the device and C(c) is concentration of silver at the capillary bed (=0). D is the diffusion coefficient of silver ($10^{-6}$) cm2/sec, d is the average distance of the device from the capillary bed (assumed to be=0.5 cm in the bone), F is Faraday's constant (96000 col./mol), and n is the charge number.

The combination of the two equations for silver diffusion gives:

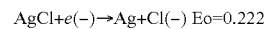

$i(Ag)=D*.n.F(C(d))/d$

Thus:

$i(Ag)=\{10^{-6})*1*(10^{-5}))*(96000)*(5*10^{-3}))/0.5\}*(1\ liter/1000\ cc)=2*10^{-9}$ Amp/cm2

The current needed to create the silver ions at the desired concentration is approximately 2 nanoAmp/cm$^2$. Similarly, the current density (A/cm2) required to reduce the chloride ions from biological level (0.1 molar) to the desired level of $2*10^{-5}$ molar could be calculated. For this equation the approximate values of the constants are D=$10^{-6}$, d=0.1 cm. The change in the Chloride concentration it assumed to be $(0.1-2*10^{-5})=0.1$. The current needed to feed the parasitic reaction can then be determined:

$i(cl)=\{(10^{-6}))*(1)*(96000)*(0.1)/(0.1)\}*(1\ lit/1000\ cc)$

=9.6*$10^{-5}$

=96 microAmp/Cm$^2$

The total anodic current needed is: i(Ag)+i (Cl)=i(anodic)= 96 microAmps/cm$^2$. On the cathode, the reaction limitation is the flux of oxygen form the source to the surface of the electrode. The max i(cathodic) current could be approximated to:

$$i(O2) = \{(0.000324)*(4)*(96000)*(5*10^{\wedge}(-3))/(0.5)\}(1\ lit/1000\ cc)$$

$$= 1.24*10^{\wedge}(-3)\ Amps/cm^2$$

Since the total cathodic current must be equal to total Anodic current:

$$i(\text{cathodic})*\text{Area of the cathode} = i(\text{anodic})*\text{Area of Anode}$$

$$=> \text{Area of the Cathode/Area of the anode} = (96*10^{\wedge}(-6))/(1.24*10^{\wedge}(-3)) = 0.077$$

This suggests that the area of the cathode must be at least equal to 8% of that of anode.

In addition to the ratio of the cathode to the ratio of the anode, another factor affecting the release of silver ions that has not previously been accounted for in galvanic release of silver to treat infection is the concentration of oxygen needed.

The concentration of the oxygen needed to power the galvanic system is typically higher than that of the equilibrium concentration, since the system must overcome the activation energy of the reactions (over-potential) and supply the additional current. In the model below we evaluated the concentration of the oxygen needed to overcome the activation energy for the reactions. Using the Tafel equation:

$$\eta = \beta \log [i/io]$$

where i=current density, η=the over-potential, 13=overpotential voltage constant, and io=intrinsic current density. For platinum, the oxygen over-potential constants are: β=0.05 volt and io=$10^{\wedge}(-9)$ A/m². Using i=$9.6*10^{\wedge}(-5)$ Amp then:

$$\eta = 0.05 \log [9.6*10^{\wedge}(-5)/(10^{\wedge}(-9))]$$

$$\eta = 0.25\ volt$$

Adding the over potential to the potential at the equilibrium (0.501 volts), and the total working half-potential needed at the cathode becomes equal to (0.501+0.25)=0.751.

Using the Nernst equation to determine the concentration of oxygen at the cathode:

$$E = 0.751 = 0.401 - (0.0592/4) \log \{[OH(-)]^{\wedge}4/[O2]\}$$

Thus, the concentration of oxygen at the electrode should be at least $7*10^{\wedge}$ (−5) mole.

The results of this analysis show that an implanted galvanic system would benefit from having an area of the cathode to the area of the anode ($A_{cathode}/A_{anode}$) of greater that about 8% and the concentration of the oxygen at the site of implant to be at least $7*10^{\wedge}(-5)$ moles per liter, which may avoid rate-limiting effect.

Thus, to address the problems and deficiencies in the prior art mentioned above, described herein are systems, methods and devices for bioabsorbable substrates that controllably release antimicrobial metal ions, including devices, systems and methods for prevent infection and for eliminating existing infections. Described below are implants including bioabsorbable substrates and methods for using them.

SUMMARY OF THE DISCLOSURE

In general, described herein are bioabsorbable substrates, and particularly bioabsorbable filaments, that galvanically release antimicrobial ions. The bioabsorbable filament is coated with an anodic metal (such as silver, copper and/or zinc) that has been co-deposited with a cathodic metal (such as platinum, gold, palladium) along at least a portion of the length of the filament. The filament retains its flexibility. After insertion into the body, the anodic metal corrodes as the filament is bioabsorbed. The degradation of the filament may create a local pH that enhances the release of the silver and/or copper and/or zinc ions.

In general, the coated filaments may be arranged into structures (e.g., sutures, mesh, slings, yarns, etc.) that can be implanted into the body.

The anodic and cathodic metals forming the coatings described herein are typically co-deposited together, and not coated in layers (e.g., atop each other). For example, the metals may be jointly vapor deposited. Examples of jointly deposited anodic and cathodic materials include silver-platinum, copper-platinum, zinc-platinum, silver-gold, copper-gold, zinc-gold, etc. Different types of jointly deposited anodic and cathodic metals may be arranged on the bioabsorble substrate. For example, silver-platinum may be coated near (either not touching or touching) a region of zinc-platinum; different co-deposited anodic/cathodic metals may be a spacer region on the substrate.

In some variations, described herein are devices and methods for preventing an infection in an implantable device such as a pacemaker or a defibrillator when inserting it into a body by incorporating bioabsorbable materials that galvanically release antimicrobial/antibacterial metals such as silver and/or zinc and/or copper. For example, an implant may be inserted into a woven mesh made of a bioabsorbable material that is coated (or impregnated) with an anti-microbial anodic metal ions such as silver or zinc co-deposited with a catalytic cathodic metal such as platinum, gold, or palladium.

In general, as mentioned above, the anodic metal may be silver, zinc, or any other metal with germicidal activity, and the cathode metal may be platinum, gold, palladium, or any other metal with catalytic action, including molybdenum, titanium, iridium, osmium, niobium and rhenium. The biodegradable substrate may be a biodegradable filament, such as polylactic acid (PLA), poly(lactic-co-glycolic acid) (PLGA), polyglycolide (PGA), polyglycoside-co-trimethylene carbonate (PGTMC), poly(caprolactone-co-glycoside), poly(dioxanone) (PDS), and poly(caprolactone) (PCL). As used herein the terms biodegradable and bioabsorbable may be used interchangeably.

For example, described herein are biodegradable filaments that may be formed into an envelope, pouch, pocket, etc. (generically, a co-implantable structure) made of a biodegradable polymer (such as PLGA, PGA, PLA, polycaprolactone, etc.). The implant may be co-implanted with the co-implantable structure, for example, by placing the mesh onto the implant before, during or after insertion into the body. The co-deposited metal coating of the co-implantable structure creates a galvanic system resulting in release of germicidal ions protecting the device from getting infected in the body once the device is implanted with the structure into a body. In the semi-aqueous environment of the body, the metal will corrode over time by releasing the ions (e.g., silver ions, copper ions, zinc ions, etc.). A coated bioabsorbable polymer could also or alternatively be used as an insert inside the lumen of the device such as a cannula, cannulated screw, or as a coating on a device. In another configuration the metal ions could be coupled with a poly-anionic (negatively charged) polymer and mixed with the polymer.

For example, described herein are bioabsorbable apparatuses that galvanically release antimicrobial ions. The apparatus may comprise: a flexible length of bioabsorbable filament; and a coating on the length of filament comprising an anodic metal that is co-deposited with a cathodic metal on the length of filament; wherein the coated filament is flexible; further wherein the anodic metal is galvanically released as antimicrobial ions when the apparatus is inserted into a subject's body.

In general, in apparatuses (systems and devices) in which the anodic metal and the cathodic metal are co-deposited (e.g., by vapor deposition) the anodic metal may be at least about 30 percent by volume of the coating. This may prevent complete encapsulation of the anodic material (e.g., zinc, silver, etc.) by the cathodic material (e.g., palladium, platinum, gold, molybdenum, titanium, iridium, osmium, niobium and rhenium). As described in greater detail below, the coatings applied may be configured to result in microregions or microdomains of anodic material in a matrix of cathodic material. The microdomains may be interconnected or networked, or they may be isolated from each other. In general, however, the concentrations of anodic material and cathodic material may be chosen (e.g., greater than 30% by weight of the anodic material, between about 30% and about 80%, between about 30% and about 70%, etc.) so that the majority of the anodic material in the coating thickness is connected to an outer surface of the coating, allowing eventual corrosion of most, if not all of the anodic metal as anti-bacterial metal ions, while providing sufficient cathodic material to provide adequate driving force for the corrosion of the anodic material. Thus, the coating may comprise the anodic metal and the cathodic metal that have been vapor-deposited onto the length of filament so that the anodic metal is not encapsulated by the cathodic metal.

As mentioned, the anodic metal may comprise zinc, copper or silver, or in some variations both zinc and silver. In general, the cathodic metal has a higher galvanic potential than the anode. For example, the cathodic metal may be one or more of: palladium, platinum, gold, molybdenum, titanium, iridium, osmium, niobium and rhenium.

As mentioned, in general the bioabsorbable substrate (e.g., filament) may comprise one or more of: polylactic acid (PLA), poly(lactic-co-glycolic acid) (PLGA), polyglycolide (PGA), polyglycoside-co-trimethylene carbonate (PGTMC), poly(caprolactone-co-glycoside), poly(dioxanone) (PDS), and poly(caprolactone) (PCL).

In general, the bioabsorbable substrate (including a length of bioabsorbable filament) is configured to degrade within the body to form a degradation product, including an anion that complexes with ions of the anodic metal and diffuses into the subject's body to form an antimicrobial zone.

The bioabsorbable substrate (e.g., bioabsorbable filament) may be configured as a mesh, bag, envelope, pouch, net, or the like, that may be configured to hold an implant. For example, the flexible structure may be configured to at least partially house a pacemaker, defibrillator, neurostimulator, or ophthalmic implant.

Also described herein are bioabsorbable apparatuses that galvanically release antimicrobial ions and comprise: a plurality of lengths of bioabsorbable filament arranged in a woven structure; and a coating on the lengths of filament comprising zinc and silver and a cathodic metal that are all co-deposited onto the lengths of filament, wherein the zinc and silver are at least about 30 percent by weight of the coating; further wherein the zinc and silver are galvanically released as antimicrobial ions when the apparatus is inserted into a subject's body. As mentioned, the woven structure may form a mesh, bag, envelope, pouch, net, or other structure that is configured to at least partially enclose an implant within the subject's body.

Also described herein are bioabsorbable apparatuses that galvanically releases antimicrobial ions and include: a plurality of lengths of bioabsorbable filament; and a coating on the lengths of filament comprising an anodic metal that is co-deposited with a cathodic metal on the lengths of filament; wherein the lengths of filament are arranged into a flexible structure; further wherein the anodic metal is galvanically released as antimicrobial ions when the apparatus is inserted into a subject's body.

Methods of forming any of these apparatuses are also described, including methods of forming a coated bioabsorbable substrate, for example, by co-depositing (vapor depositing) an anodic material and a cathodic material onto the substrate. The substrate may be a fiber or the structure formed of the fiber. In some variations the method may also include forming different regions of co-deposited anodic and cathodic materials, wherein the different regions include different combinations of anodic and cathodic materials. The different regions may be non-contacting. In general, co-deposing anodic and cathodic materials are typically performed so that the anodic material forms greater than 30% by weight of the coating, preventing encapsulation of the anodic material by cathodic material within the coating.

Also described are methods of treating a subject using the bioabsorbable materials that are co-deposited with one or more coating of anodic and cathodic materials. For example, described herein are methods of galvanically releasing antimicrobial ions to form an antimicrobial zone around an implant that is inserted into a subject's tissue. The method may include step of: inserting into the subject's tissue an apparatus comprising a plurality of lengths of bioabsorbable filament having a coating comprising an anodic metal and a cathodic metal that are co-deposited onto the lengths of filament, wherein the implant is at least partially housed within the apparatus; galvanically releasing antimicrobial ions from the coating (e.g., galvanically releasing ions of silver and zinc); allowing the lengths of filament to degrade into a degradation product including anions, wherein the anions complex with antimicrobial ions of the anodic metal and diffuse into the tissue to form an antimicrobial zone around the implant. The method may also include inserting an implant into the apparatus before the apparatus is inserted into the subject's body. For example, inserting the apparatus into the body may comprise inserting a flexible apparatus comprising the plurality of length of bioabsorbable filaments forming a bag, envelope, pouch, net or other structure (woven or otherwise) formed to hold the implant. For example, the method may also include inserting a pacemaker, a defibrillator or a neurostimulator into the apparatus.

Inserting the apparatus may comprise inserting the apparatus having a plurality of lengths of bioabsorbable filaments coated with the anodic metal that comprises silver and zinc that are co-deposited onto the lengths of filament with the cathodic metal.

Allowing the lengths of filament to degrade may comprise degrading the lengths of filament into anions that bind to silver ions from the coating. For example, inserting the apparatus comprises inserting the apparatus having a plurality of lengths of bioabsorbable filaments coated with the anodic metal that is co-deposited onto the lengths of filament with the cathodic metal, wherein the anodic metal is at least about 30 percent by weight of the coating.

Inserting the apparatus comprising the plurality of lengths of bioabsorbable filament may comprise inserting the apparatus having a plurality of lengths of one or more of: polylactic acid (PLA), poly(lactic-co-glycolic acid) (PLGA), and polyglycolide (PGA).

In general, the antimicrobial zone around the implant may be sustained for at least seven days.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 8A is a side perspective view of one example of a plug or patch that may be used, e.g., to repair a hernia. The device is coated with multiple types of combined coatings for galvanic release of metal ions.

FIG. 8B shows an enlarged view of one region of the plug.

FIG. 9 is a perspective view of one variation of a bandage or patch including a combined coating, shown on a patient's knee.

DETAILED DESCRIPTION

In general, described herein are apparatuses (e.g., systems and devices) that include a bioabsorbable substrate and that galvanically release antimicrobial ions over an extended period of time. The bioabsorbable substrate may degrade during the same period that the antimicrobial ions are being released (e.g., days, months, years). In general the bioabsorbable substrate is coated with a combination of anodic metal, such as silver and/or zinc and/or copper, and a cathodic metal, such as palladium, platinum, gold, molybdenum, titanium, iridium, osmium, niobium and rhenium, where the anodic metal and cathodic metals are co-deposited (e.g., by vapor deposition) so that the anodic metal is exposed to an outer surface of the coating and not fully encapsulated in the cathodic metal, and there is sufficient cathodic metal to drive the galvanic release of anodic ions when implanted into the body (e.g., when exposed to body regions containing bodily fluids such as blood, lymph, etc.).

For example, described herein are bioabsorbable substrates onto which anodic metal and cathodic metals are co-deposited to form a coating, allowing the anodic metal to be galvanically released as ions (e.g., antimicrobial silver, copper and/or zinc ions) when the apparatus is inserted into the subject's body.

In general, the bioabsorbable substrate may be formed as a flexible filament, and the coating of anodic and cathodic metals that may corrode to release anodic ions may allow the flexible filament to remain flexible. Galvanic release results in degradation (e.g., corrosion) of the coating.

Figure 1A:
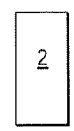
FIGS. 1A-1F illustrate the general concept of galvanic release of silver ions.
Figure 1B:
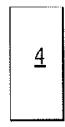
Figure 1C:
Figure 1D:
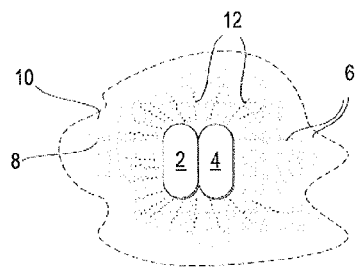
Figure 1E:
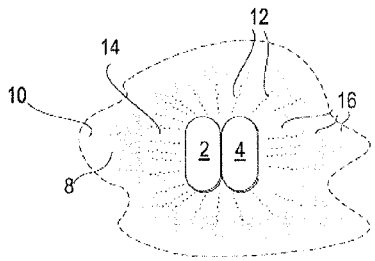
Figure 1F:
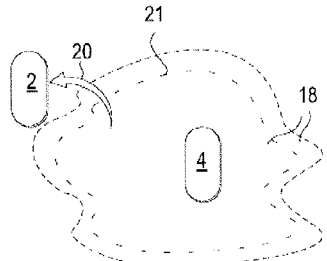

FIGS. 1A-1F describe a simple galvanic cell setup such as for use in a body. The setup is shown treating an infection, but the same process could be applied to healthy tissue to prevent an infection (prophylactically). The components including a first metal 2 (e.g., silver), second metal 4 (e.g., platinum), and electrolytic fluid 6 (e.g., blood) are shown individually in FIGS. 1A-1C and arranged in a tissue in FIGS. 1D-1F. Electrolytic body fluid 6 is shown bathing or contacting healthy tissue 10 as well as infected tissue 8. When silver metal 2 contacts platinum metal 4 in body fluid 6, it forms a galvanic cell with a silver anode and platinum cathode. As shown in FIG. 1E, ionic silver 12 is generated and spreads through the body fluid, killing microorganisms and creating an infection-free zone 14 in body fluid 16 in the vicinity of the anode. After treatment is complete, the silver anode 2 may be completely corroded 20 leaving an infection-free body fluid 18. Any metal with a higher redox potential than silver may be used as the cathode. The metal may be a noble metal, such as gold, palladium or platinum. Although the example shown in FIG. 1A-1F describes using a silver metal anode that is placed adjacent to a platinum metal cathode, described herein are coatings in which the anodic metal (e.g., silver, zinc, copper) is co-deposited onto a biodegradable substrate.

In general, a coating of anodic metal and cathodic metal may be configured so that the anodic metal and cathodic metal are within the same layer. The microregions of anodic metal may be embedded within the cathodic metal, including being embedded within a matrix of cathodic metal (or vice versa). As illustrated below, the microdomains or microregions of anodic metal that are within a cathodic matrix, allowing a large spatial release pattern of anodic metal ions by galvanic action triggered by the contact of the anodic metal and the cathodic metal within the electrolytic bodily fluid. The coatings described herein, in which the anodic metal and the cathodic metal are combined as part of the same layer may be referred to as "combined" coatings, in which an anionic metal and a cationic metal are both jointly coated.

The combined coatings described herein may be non-uniform mixtures of anodic and cathodic metals. For example, the anionic metal may form microregions or microdomains within the cationic metal (or vice versa). In general, the cathodic metal microdomains may form one or more (typically a plurality) of continuous paths through the cathodic metal. For example, the microdomains described herein may be veins, clusters, threads, clumps, particles, etc. (including interconnected veins, clusters, threads, clumps, particles, etc.) of anodic metal, e.g., silver, copper, or zinc, that are connected to an outer surface of the coating, so that they are exposed to the electrolytic bodily fluid (e.g., blood). The microdomains of anodic metal may form a network within the matrix of the cathodic metal. Thus, the anodic metals may be present in one or more networks that are electrically connected within the cathodic matrix. The individual sizes of particles, threads, branches, veins, etc. forming the microdomains may be small (typically, e.g., less than a 1 mm, less than 0.1 mm, less than 0.01 mm, less than 0.001 mm, less than 0.0001 mm, less than 0.00001 mm, etc.). Similarly, in some variations the matrix may be the anodic metal and the cathodic metal may be referred to as forming microdomains (e.g., where the percentage of cathodic metal in the coating is less than 50%, less than 45%, less than 40%, less than 30%, etc. by weight of the coating).

A combined anodic metal and cathodic metal forming a combined coating (or a portion of a coating) may be formed of a single anodic metal (e.g., silver) with a single cathodic metal (e.g., platinum), which may be referred to by the combined anodic metal and cathodic metals forming the coating or portion of a coating (e.g., as a combined silver/platinum coating, a combined silver/palladium coating, a combined zinc/platinum coating, a combined zinc/palladium coating, etc.). In some variations a combined coating may include multiple anodic and/or cathodic metals. For example, the combined coating may include zinc and silver co-deposited with platinum.

In general, the anodic metal in the combined coating may include a continuous path connecting the anodic metal to an exposed outer surface of the coating so that they can be galvanically released from the coating. Deeper regions (veins, clusters, etc.) of the anodic metal may be connected to more superficial regions so that as the more superficial regions are corroded away by the release of the anodic ions, the deeper regions are exposed, allowing further release. This may also expose additional cathodic metal. Thus, in general, anodic metal microdomains are not completely encapsulated within the catholic metal. In some variations, the majority of the anodic metal is not completely encapsulated within the cathodic metal, but is connected to an exposed site on the surface of the coating via connection through a more superficial region of anodic metal; although some of the anodic metal may completely encapsulated. For example, the coating may include an anodic metal in which less than 50 percent of the total anodic metal is completely encapsulated within the cathodic metal (e.g., less than 40%, less than 35%, less than 30%, less than 25%, less than 20%, less than 15%, less than 10%, etc.).

The co-deposited anodic and cathodic combined coatings described herein for the galvanic release of anodic ions may be formed by co-depositing the anodic metal and the cathodic metal so as to minimize the amount of encapsulation by the cathodic material. For example, the percentage of the anodic material may be chosen so that there is both an optimal amount of cathodic metal to drive reasonable galvanic release in the presence of an electrolyte, and so that there is sufficient continuity of anodic metal with the combined coating to form a continuous path to an exposed surface of the coating, making it available for galvanic release. For example, a coating may be formed by co-depositing the anodic metal and the cathodic metal (e.g., sputtering, vapor deposition, electroplating, etc.) where the concentration of the anodic metal is high enough to allow the formation of a sufficient number of continuous paths through the thickness of the coating. We have found that a combined coating in which more than 30% (by weight) of the coating is formed of the anodic metal is sufficient to form a combined coating with a cathodic metal in which more than half (e.g., >50%) of the anodic metal is connected by a continuous path to the surface of the coating, permitting galvanic release. Thus less than half of the anodic metal is fully encapsulated by the non-corroding cathodic metal and trapped within the coating. Thus, in general, the combined coatings (also referred to as co-deposited coatings) may include more than 25% (e.g., 30% or greater, 35% or greater) of anodic metal that is co-deposited with the cathodic metal. The remainder of the coating (e.g., between 5% and 75%) may be cathodic metal. Thus, the percent of anodic metal co-deposited with cathodic metal may be between 25%-95% (e.g., between about 30% and about 95%, between about 30% and about 90%, between about 30% and about 80%, between about 30% and about 70%, etc.), with the remainder of the coating being cathodic metal.

The coatings described herein may be of any appropriate thickness. For example, the coatings may be between about 500 microinches and about 0.01 microinches thick, or less than about 200 microinches, less than about 150 microinches, less than about 100 microinches, less than about 50 microinches, etc. The thickness may be selected based on the amount and duration (timing) of the release of anodic metal. In addition, the coatings may be patterned, e.g. so that they are applied onto a substrate in a desired pattern, or over the entire substrate. As mentioned and described further below, different combined coatings may be applied to the same substrate. For example, a combined coating of silver/platinum may be applied adjacent to a combined coating of zinc/platinum, etc. The different combined coatings may have different properties (e.g., different anodic metal, different anodic/cathodic metal percentages, different thicknesses, etc.) and therefore different release profiles. Combinations in which different combined coatings are in (electrical) contact with each other may also have a different release profile than combinations in which the different coatings are not in electrical contact. For example, a material may include a first combined coating of zinc and an cathodic metal (e.g., zinc/platinum) and a second combined coating of silver and a cathodic metal (e.g. silver/platinum). If the first and second combined coatings are in electrical contact, the zinc will be galvanically released first. If the first and second combined coatings are not in electrical contact, then both zinc and silver will be concurrently released (though zinc may be released more quickly and my diffuse further).

Figure 2A:
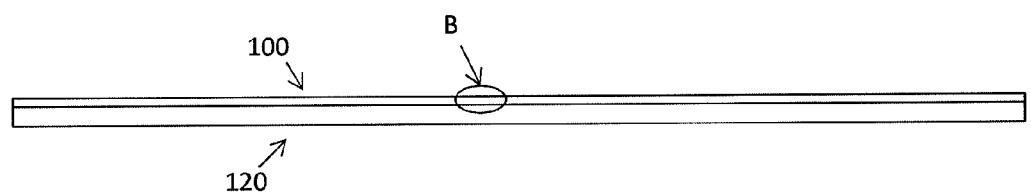
FIG. 2A shows a cross-sectional view through one example of a substrate having a combined coating, comprising an anodic metal that is co-deposited with a cathodic metal.

For example, FIG. 2A illustrates one example of a substrate 120 onto which a combined coating of anodic and cathodic metals have been co-deposited 100. The substrate may be, in particular, a bioabsorbable material. Although the combined coatings described herein may be used with any substrate (even non-bioabsorbable substrates), any of the examples described herein may be used with bioabsorbable substrates. In the example of FIG. 2A the dimensions (thicknesses of the substrate and coating) are not to scale. For example, the coating may be less than 100 microinches thick. The substrate may be any appropriate thickness. In FIG. 2A, region B shows an enlarged portion of the coating and substrate, which is illustrated in FIG. 2B.

Figure 2B:
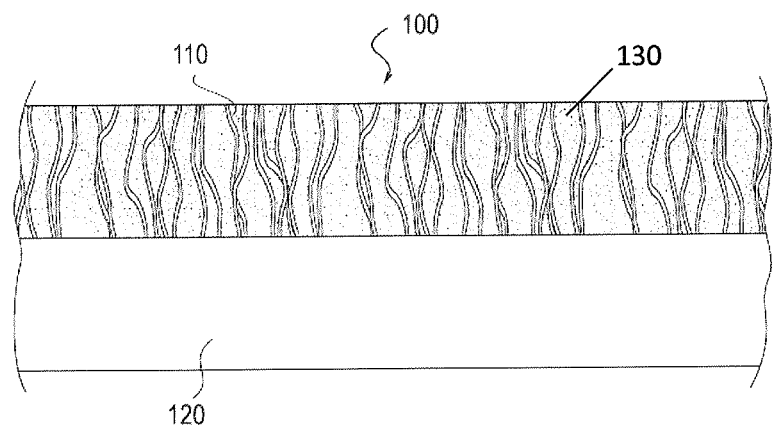
FIG. 2B is a schematic representation of an enlarged view of a portion of the coated substrate of FIG. 2A.
Figure 2C:
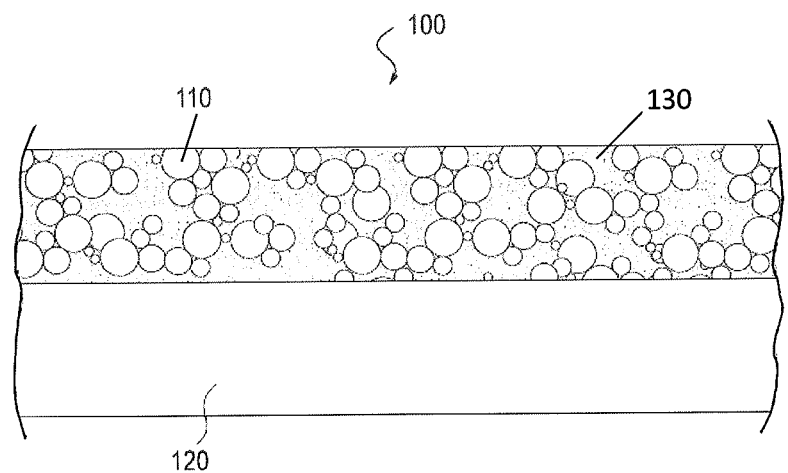
FIG. 2C is another schematic representation of an enlarged view of a portion of the coated substrate of FIG. 2A.

In FIG. 2B, a portion of the substrate 120 (e.g. a bioabsorbable substrate) is shown coated with a combined coating 100. The anodic metal, e.g., silver, 110 is shown forming veins or microregions within the cathodic metal 130. In this example, the silver is schematically illustrated as forming veins through a matrix of cathodic metal, e.g., platinum. The actual microdomains may be much smaller, and filamentous; for example, the microdomains may be on the order of 10-1000 Angstroms (or more) across. FIG. 2C is another schematic illustration of a section through a portion of a combined coating on a substrate, showing microdomains of anodic metal (e.g. silver) 110, within a matrix of cathodic metal (e.g., platinum) 130. In FIGS. 2B and 2C the majority of the microdomains of anodic metal are connected in a continuous path to the outer surface of the coating 100, allowing galvanic release of the anodic material.

Figure 2D:
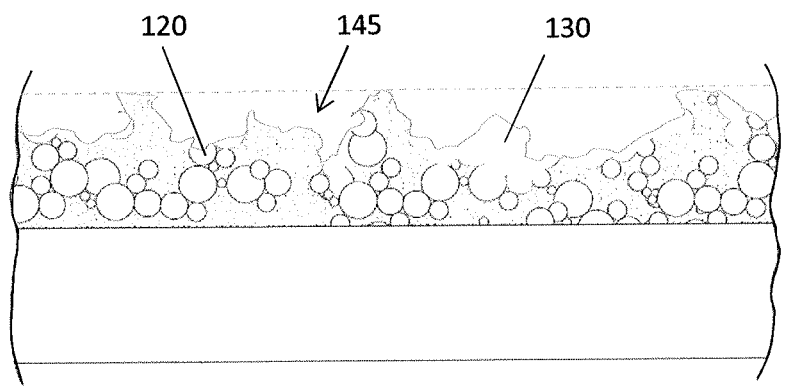
FIG. 2D is an example of the galvanic release (and corrosion) of a coating on a substrate such as the one shown in FIG. 2A.

FIG. 2D illustrates an example of the coating of FIG. 2C during the galvanic release process, in which the implant including the substrate and the combined coating is place into the body, so that the coating is exposed to blood. As shown in FIG. 2D, the anodic metal (silver) in the coating is progressively corroded as ions of silver are released into the body to locally diffuse and provide regional antimicrobial treatment. In this example the anodic metal (e.g., silver) 120 exposed to the surface is release, leaving a negative impression in the cathodic metal 130. Regions of the cathodic metal that are left behind may remain coated (though the substrate may also be biodegrading simultaneous with the release of anodic metal, not shown). Typically, the coating layer is thin enough that any remaining cathodic metal (e.g., platinum) is small enough to be ignored or easily cleared by the body.

The combined layers are generally formed by co-depositing the anodic metal and the cathodic metal onto the substrate. For example, a combined layer may be formed by simultaneously sputtering the two metals onto the substrate to the desired thickness. For example, both silver and platinum may be placed into a sputtering machine and applied to the substrate. The amount of cathodic material and anodic material may be controlled, e.g., controlling the percentage of the coating that if anodic metal and the percentage that is cathodic (e.g., 40% anodic/60% cathodic). This sputtering process results in a non-uniform pattern, as discussed above, and illustrated in FIGS. 2B-2C, when observed at high magnitude. Alternatively, combined layers may be formed by vacuum deposition, or any other technique that can co-deposit the two (or more) metals onto the substrate. Formation of the coating(s) may include masking, for example, locating coatings in particular regions of the substrate.

Thus, in general, any of the substrates (e.g., bioabsorbable substrates) described herein may be applied in a pattern, including patterns of multiple different combined coatings. Further, coatings may be applied over only apportion of the substrate, which may allow more localized release of the antimicrobial ions and may prevent the coating from interfering with the properties of the substrate and/or the device that the substrate is part of (e.g., flexibility, surface characteristics, etc.). For example, FIGS. 3A-3C show a top view of a substrate coated with various combined coatings (co-deposited anodic and cathodic metals).

Figure 3A:
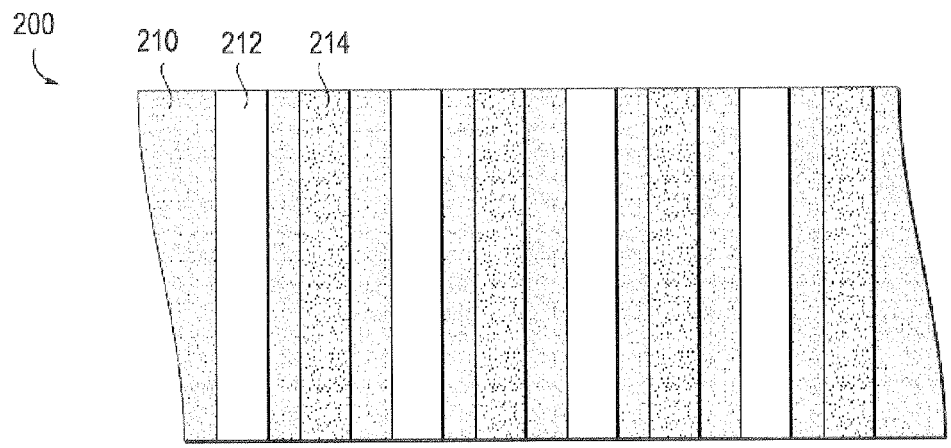
FIGS. 3A-3C illustrate top views of alternative variations of coating patterns for different combined coatings, such as silver/platinum and zinc/platinum.
Figure 3B:
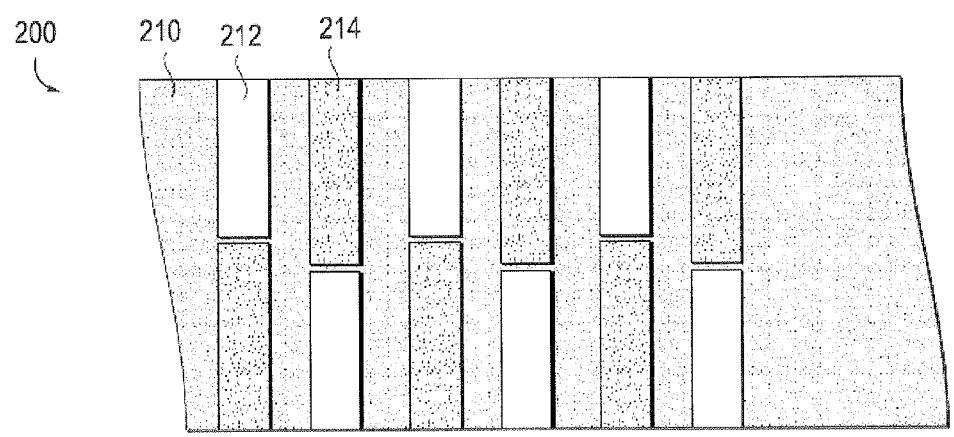

For example, in FIG. 3A, the surface of the substrate 210 of an implant 200 that includes alternating patterns of a first combined coating 212 of silver/platinum that have been co-deposited onto the substrate and a second combined coating 214 of zinc/platinum co-deposited onto the substrate. In this example the first and second coating regions are formed into strips extending along the width of the substrate; the first and second coating regions do not overlap and are not in electrical contact with each other. Thus, the silver ions in the first coating region(s) 212 will be galvanically released concurrently with the zinc ions galvanically released from the second coating region(s) 214 when exposed to an electrolytic bodily fluid (e.g., blood), corroding the two layers. FIG. 3B shows another example of a pattern of a first combined coating 212 (e.g., silver/platinum) and a second combined coating 214 (zinc/palladium) that are arranged with alternating stripes on the surface of the substrate 210, where the stripes are end-to-end with each other.

Figure 3C:
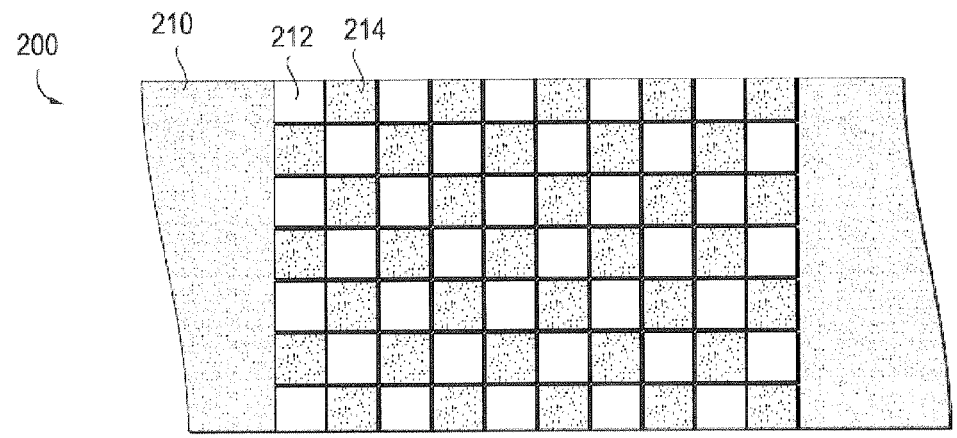

FIG. 3C shows another variation of a surface 210 of an implant 200 that includes a pattern, shown as a checkerboard pattern, of first and second combined coatings. In FIG. 3C, the edges of the different coating regions may contact each other or may be separated by a channel so that they are not in electrical contact for the galvanic reaction. For example, if the first and second regions do contact each other so that they are in electrical contact, then the galvanic reaction may drive the release of the zinc ions before the release of the silver ions; once the zinc has corroded, the silver ions may be released.

In general, there may be some benefit to including multiple coatings, and in particular coatings having multiple anodic metals. The antimicrobial region around the coated implant may be made larger and the ions may be released over a longer time period, than with a single type of anodic coating alone.

As mentioned, the combined coatings of co-deposited anodic and cathodic metals could be formed in any pattern.

The substrate onto which the combined coatings may be applied may be any appropriate substrate, and in particular, may be a bioabsorbable substrate. Examples of bioabsorbable materials that may be used includes polymeric materials such as: polylactic acid (PLA), poly(lactic-co-glycolic acid) (PLGA), polyglycolide (PGA), polyglycoside-co-trimethylene carbonate (PGTMC), poly(caprolactone-co-glycoside), poly(dioxanone) (PDS), and poly(caprolactone) (PCL), and combinations of these.

In general, bioabsorbable materials for medical applications are well known, and include bioabsorbable polymers made from a variety of bioabsorbable resins; for example, U.S. Pat. No. 5,423,859 to Koyfman et al., lists exemplary bioabsorbable or biodegradable resins from which bioabsorbable materials for medical devices may be made. Bioabsorbable materials extend to synthetic bioabsorbable or naturally derived polymers.

For example, bioabsorbable substrates may include polyester or polylactone selected from the group comprising polymers of polyglycolic acid, glycolide, lactic acid, lactide, dioxanone, trimethylene carbonate, polyanhydrides, polyesteramides, polyortheoesters, polyphosphazenes, and copolymers of these and related polymers or monomers. Other bioabsorbable substrates may include substrates formed of proteins (e.g., selected from the group comprising albumin, fibrin, collagen, or elastin), as well as polysaccharides (e.g., selected from the group comprising chitosan, alginates, or hyaluronic acid), and biosynthetic polymers, such as 3-hydroxybutyrate polymers.

The bioabsorbable substrate may be absorbed over a predetermined time period after insertion into a body. For example, the bioabsorbable substrate may be absorbed over hours, days, weeks, months, or years. The substrate may be bioabsorbed before, during or after release of the anodic metal ions from the combined coating. In some variations the release of the antimicrobial ions is timed to match the degradation/absorption of the substrate. Further, the absorption of the substrate may facilitate the release of the anodic metal ions. For example, some of the bioabsorbable substrates described herein may result in a local pH change as the substrate is bioabsorbed; the release of the metal ions may be facilitated by the altered pH.

Figure 4:
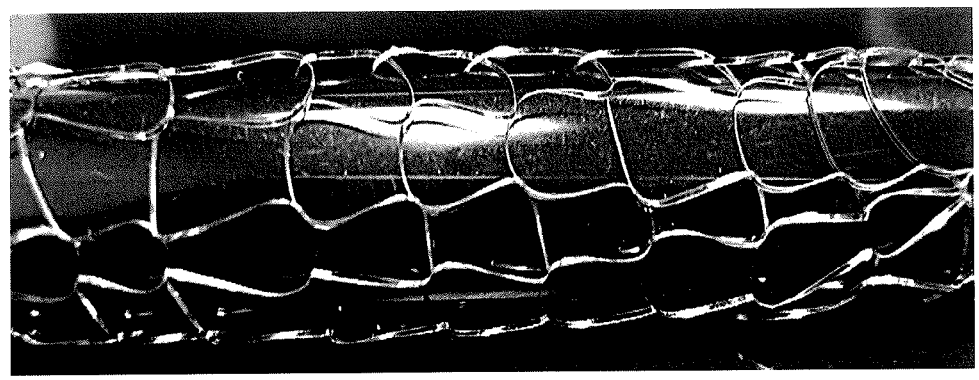
FIG. 4 is an example of a bioabsorbable pouch woven from one or more strands, wherein the strands of the pouch are coated with the combined coatings described herein for release of antimicrobial ions.

FIG. 4 shows an example of a pouch device formed from woven lengths of bioabsorbable filament that is flexible. The filament is formed of a bioabsorbable polymer, PGLA, and this bioabsorbable substrate has been coated with the combined anodic metal/cathodic metal coating described above. In FIG. 4A, the pouch of PGLA fibers coated with (e.g., by vapor deposition) co-deposited silver and platinum galvanically releases silver ions after insertion into the body. The release of anodic metal ions (e.g., silver ions) is enhanced as the bioabsorbable substrate (e.g., PGLA) is hydrolyzed. Hydrolysis lowers the local pH and this may increase solubility of silver and bio-absorption.

The pouch of FIG. 4 may be used similarly to those described in U.S. Pat. No. 8,591,531, herein incorporated by reference in its entirety.

In general, the bioabsorbable substrate may be formed into any appropriate shape or structure. For example, a bioabsorbable substrate may be a filament that is coated, completely or partially, by one or more of any of the combined coatings of anodic and cathodic metals co-deposited onto the bioabsorbable substrate. Coated strands (e.g., filaments, strings, wires, etc.) of bioabsorbable substrate may be used by themselves, e.g., as suture, ties, etc. within a body, or they may be used to form 2D or 3D implants, for example, by weaving them. The combined coatings described herein may be coated onto these structures either before or after they have been formed. For example, a coated filament may be woven into a net (or into a pouch for holding an implantable device, as shown in FIG. 4), or the filament may be woven into a net and then coated.

Figure 5:
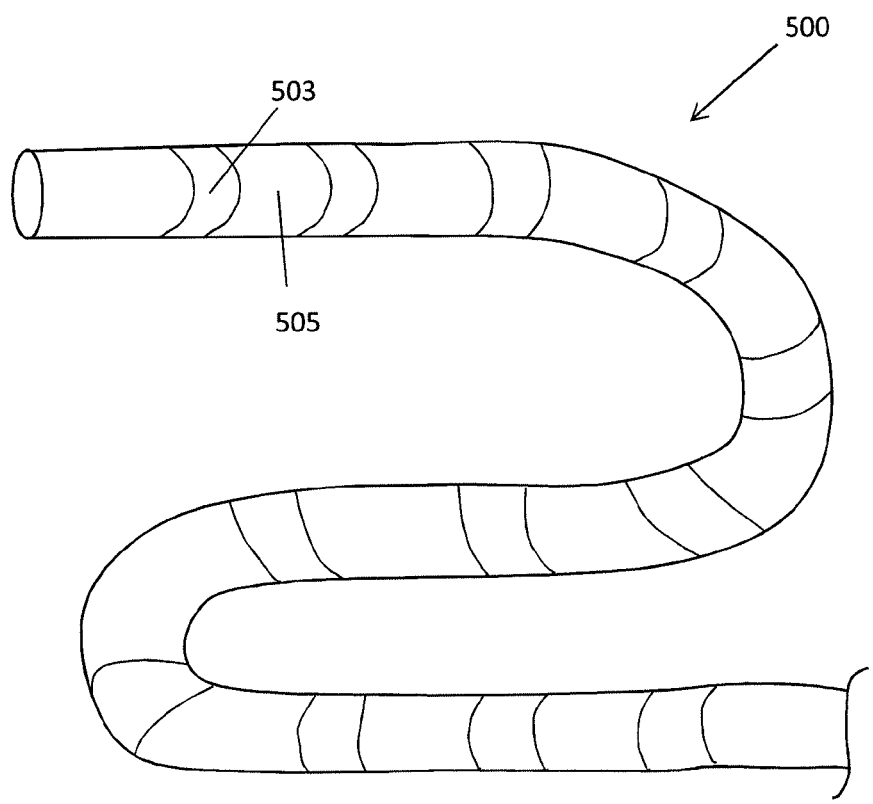
FIG. 5 illustrates a fiber or filament (e.g., suture fiber) coated with a striped pattern of a combined coating for galvanic release of metal ions.
Figure 6:
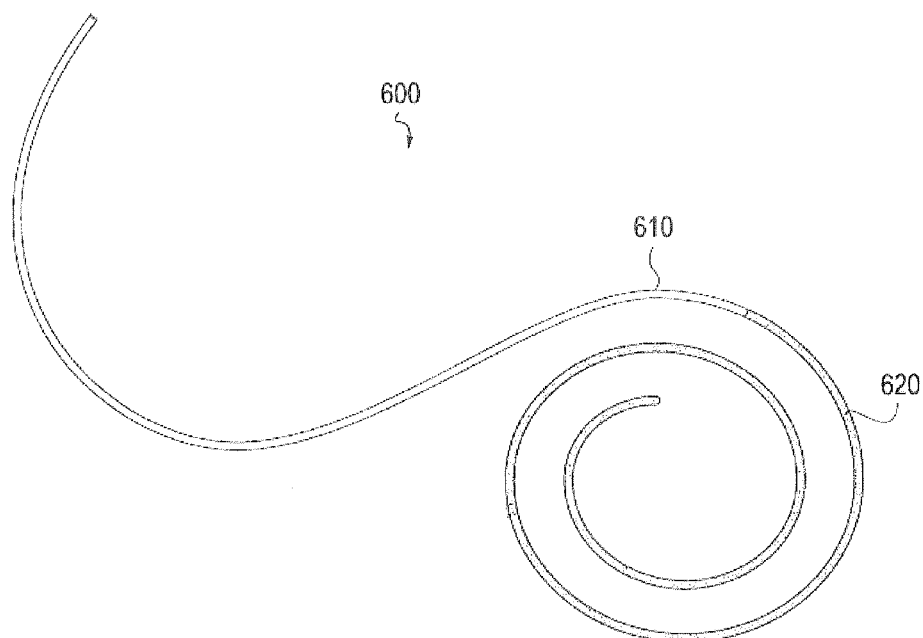
FIG. 6 is an example of a length of suture formed from a bioabsorbable substrate onto which a combined coating has been regionally applied (e.g., near the distal end).

FIG. 5 shows an example of a filament that may be formed of a bioabsorbable substrate that is coated with a combined anodic/cathodic metal coating for galvanic release of anodic metal ions. In FIG. 5, the fiber 500 may include uncoated regions 505 alternating with coated regions 503. The coated region(s) may be a spiral shape around the fiber, a ring around the fiber (as shown in FIG. 5) or any other pattern. Multiple coatings may be used (see, e.g., FIGS. 3A-3C). The coated fiber may retain its flexibility. In some variations the fiber may be used, e.g., as a suture. FIG. 6 shows another example of a suture 600 that is coated 620 over the distal portion of the suture, which may be used in the body. The suture may be pre-loaded on a device (including an implant, needle, etc.). The suture may be formed of a bioabsorbable substrate 610 onto which the coating is applied.

In any of the devices described herein, the coating may be made directly onto the bioabsorbable substrate. In some variations the coating may be made on top of another coating (e.g., a primer coating) which may be made to prepare the substrate for the coating.

Figure 7:
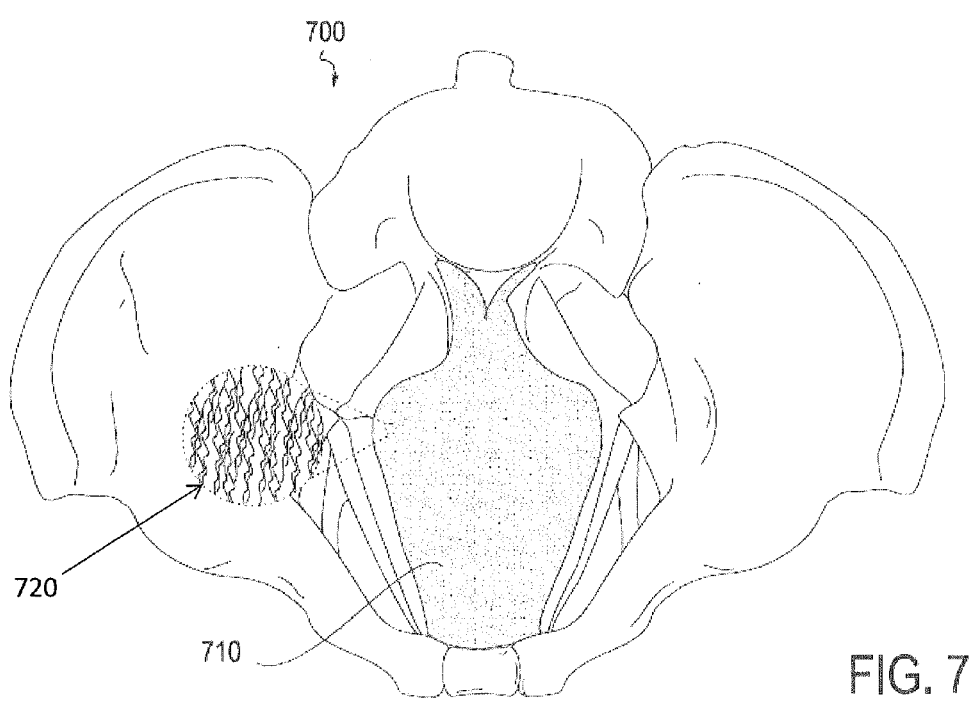
FIG. 7 illustrates one example of a medical device configured as a transvaginal mesh having a combined coating for release of metal ions after insertion into the body.

Additional examples of woven structures are shown in FIGS. 7-11. In FIG. 7, the device 700 is formed of filaments 710 woven or arranged into a mesh (shown in the enlarged view 720) that are coated with a combined coating (or multiple types of combined coatings) as described herein. In this example, the mesh formed is configured as a transvaginal mesh (intravaginal mesh) that may be used for the treatment of vaginal prolapse, for example. Slings or other anatomical support structures, either durable or biodegradable, could also be formed. These devices may galvanically release one or more type of anionic metal ion having antimicrobial effect. For example the mesh may be coated with a coating of silver/platinum that is co-deposited onto the mesh or the fibers forming the mesh for galvanic release of silver from the coating.

FIGS. 8A and 8B illustrate another example of a structure, shown as a woven structure, that may also be configured as a non-woven (e.g., solid) structure. In FIG. 8A the device 400 is a patch or plug that may be used for treating a hernia. In this example, the patch is a woven mesh that includes two types of combined coatings: silver/platinum and zinc/platinum in different regions over the surface of the patch. Darker regions 803 may indicate the silver/platinum co-deposited coating regions, while the lighter regions 805 represent co-deposited zinc/platinum regions. The entire patch outer surface or only a portion of the outer surface may be coated; in FIG. 8A, only discrete regions are shown as coated, for the sake of simplicity. FIG. 8B shows an enlarged view illustrating the fibers forming the weave of the patch. As shown in FIG. 8B, only some of the fibers are coated (e.g., every other fiber of the warp); in some variations, alternating fibers in one direction (warp) are coated with different anodic/cathodic metals, while fibers in the opposite direction (weft) are uncoated.

FIG. 9 illustrates another example of a woven material, formed of a bioabsorbable fiber, coated with the combined coatings described herein for galvanic release of antimicrobial metal ions. In FIG. 9, the device is a patch that could be used, e.g., within the knee after surgery, to reduce the chance of infection. In this example, as in FIGS. 8A and 8B above, the patch may include filaments/fibers having different coatings (e.g., silver/platinum, zinc platinum, silver palladium, zinc palladium, etc.) and/or different regions on the patch, as shown by the light and darker regions in FIG. 9. In some variations the patch may be worn outside of the body, e.g., it is "implanted" by placing it over a wound, rather than entirely within the body. Blood in the wound region may act as the electrolytic fluid, allowing galvanic release of the metal ions.

Figure 10:
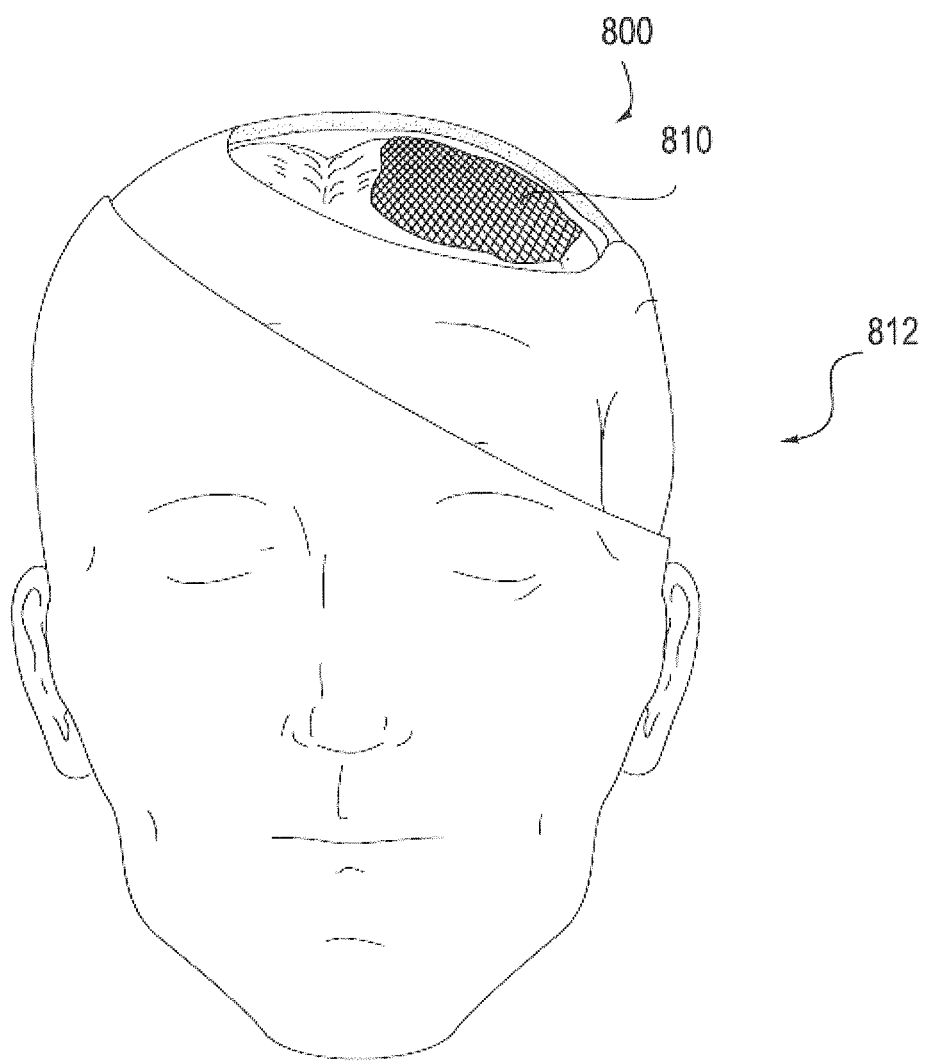
FIG. 10 illustrates one variation of an artificial dura (mesh) including a combined coating for galvanic release of metal ions.

Similarly, FIG. 10 illustrates a dural replacement mesh 810 that may be implanted into a subject's head 812 to replace dural matter following trauma and/or surgery. The mesh may be formed of a non-bioabsorbable material (or a bioabsorbable material) that is coated as described above so as to galvanically release antimicrobial metal ions.

Figure 11:
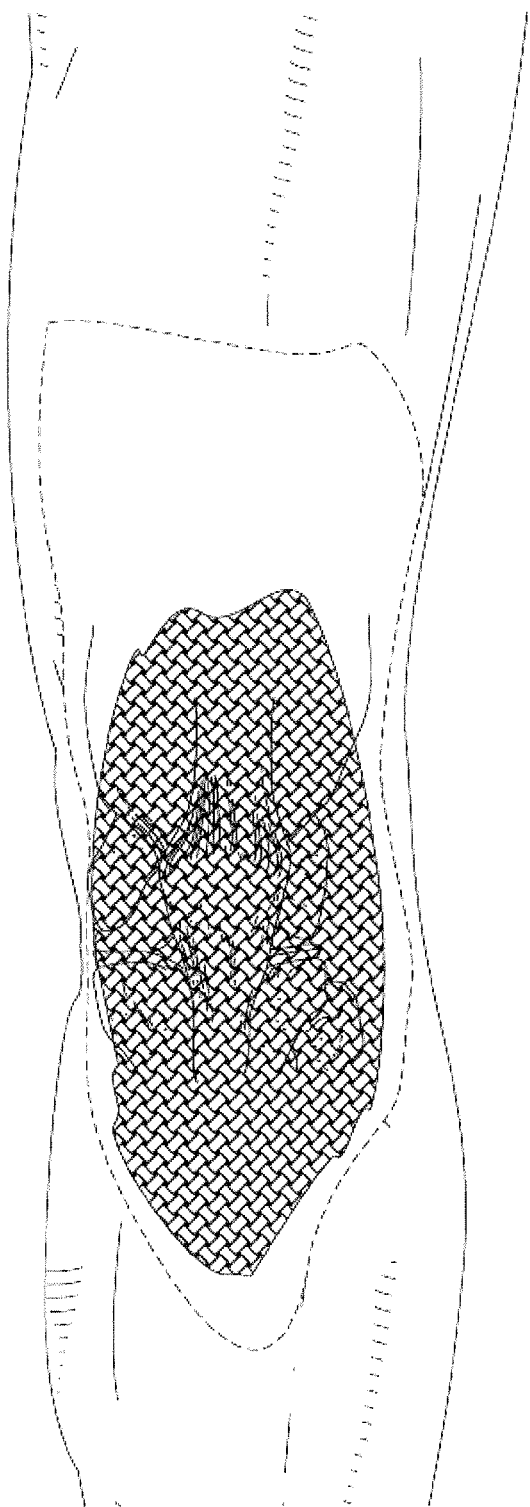
FIG. 11 shows an example of a material that may be used as within a wound or surgical site to prevent or treat infection. The material may be a porous and/or bioabsorbable mesh that is configured to galvanically release metal ions.

FIG. 11 illustrates another example of a fabric or mesh that may be implanted into a patient as part of a surgical procedure. In FIG. 11, the mesh is a woven fabric that has been coated with one or more combined coatings of anodic and cathodic metals co-deposited on the substrate (e.g., bioabsorbable substrate) for galvanic release of metal ions. The material may be used, for example, as part of a large joint procedure such as knee replacement, or spinal surgery (e.g., fixation using rods, screws, etc.) in place of currently used antibiotic powers. For example the coated bioabsorbable mesh could be in, around, or over the surgical site and used to galvanically release antimicrobial ions following surgery. The implant (material) would break down over time, and be absorbed following implantation (e.g., within 30 days following the procedure), allowing sufficient time for the patient to recover and avoid infection potentially introduced by the procedure and/or the resulting wound.

Although the devices described herein include flexible, e.g., filament or mesh, structures, the devices may also be configured as rigid or more traditional surgical implants, including screws, rods, staples, cannulas, etc. The substrate may be bioabsorbable.

Figure 12A:
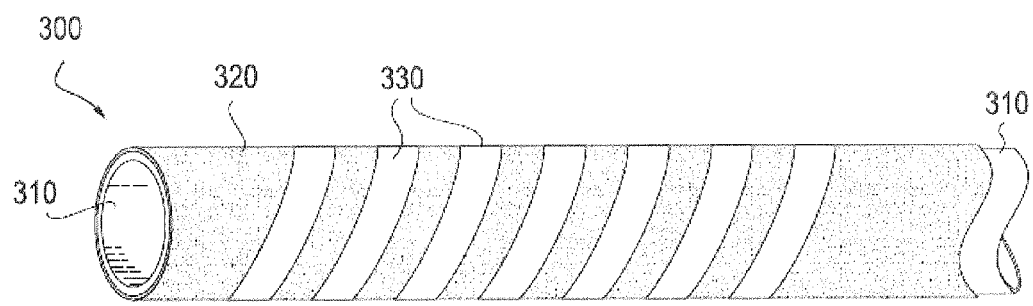
FIGS. 12A and 12B show side perspective and end views, respectively of one variation of a cannula including a pattern of a combined coating for the release of antimicrobial metal ions.
Figure 12B:
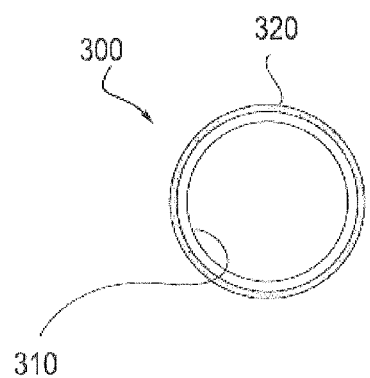

For example, FIGS. 12A-12B shows one variation of a cannula that may be used within a body and galvanically release antimicrobial metal ions. In FIG. 12A, the cannula 300 includes a substrate 320 onto which a combined coating 330 is applied in a spiral pattern. The combined coating galvanically releases anodic metal ions (e.g., silver, zinc, copper), is includes the anodic metal that has been co-deposited with cathodic metal (e.g., platinum, palladium, etc.). In this example, the inner surface 310 of the cannula 300 may also be separately coated with a combined coating (the same or a different coating). FIG. 12B shows a side view of the catheter of FIG. 12A.

Any of the devices described herein may be used as part of a surgical procedure within a body (e.g., human, animal, etc.). In general, the combined coatings described herein may be implanted into the body and may galvanically release metal ions over an extended period of time (e.g., days, weeks, months). For example, in some variations the coating and/or apparatus (e.g., device) may be configured to galvanically release metal ions for 30 days, 60 days, 90 days, or more.

The anti-microbial coatings, devices and systems described herein may use two or more types of metal ions with anti-microbial properties, such as silver and zinc. The zone of inhibition of microbial activity/growth formed around the coated devices due to the released metal ions may be enhanced where two different types (e.g., silver and zinc) are released. The combination of zinc and silver has been observed to have a synergistic effect compared to either metal alone.

Further, when the combined coatings described herein are used in combination with the bioabsorbable (e.g., biodegradable) substrates or material, the metal ions may form complexes with the byproducts of degradation of the substrate (e.g., polymeric substrates including PLA, PLGA, PGA) such as lactate, galactate, or glucoate. These substrates may increase the anti-microbial activity. For example, the range of diffusion of the anionic metal ions (e.g., zinc, silver, etc.) may be increased by the creation of a complex between the metal ions and the polymeric degradation byproduct. Further, as mentioned above, degradation of the polymers may create acidic byproducts such as lactic acid, galactic acid, and/or glycolic acid. The drop in pH and formation of the anionic byproducts may further enhance the rate of the galvanic reaction.

Thus, the apparatuses and methods above may generally take advantage of the use of bioabsorbable substrates that are coated through a co-deposition process of a cathodic metal (e.g., platinum, palladium, gold, etc.) and an anodic metal (e.g., silver, zinc, copper) to form a galvanic circuit in a fluid (e.g., electrolytic) medium to create an antimicrobial zone. The degradation of the bioabsorbable substrate may further enhance this antimicrobial zone, e.g., by forming complexes with the released metal ions to further diffuse the ions as well as to alter the local pH to enhance the galvanic reaction. In general, as described above, the combined coatings described herein can be quite thin and do not compromise the flexibility, chemic structure, strength (e.g., tensile strength) or chemical properties of the underlying substrate(s).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A bioabsorbable apparatus that galvanically releases antimicrobial ions, the apparatus comprising:
    a flexible length of bioabsorbable filament; and
    a coating on the length of filament comprising an anodic metal that is co-deposited with a cathodic metal on the length of filament to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal within the matrix of cathodic metal or a continuous path of cathodic metal within the matrix of anodic metal, wherein the continuous path extends from an outer surface of the coating to the filament;
    wherein the coated filament is flexible;
    further wherein the anodic metal is galvanically released as antimicrobial ions when the apparatus is inserted into a subject's body.

2. The apparatus of claim 1, wherein the anodic metal is at least about 30 percent by volume of the coating.

3. The apparatus of claim 1, wherein the anodic metal comprises both zinc and silver.

4. The apparatus of claim 1, wherein the anodic metal comprises silver, zinc or copper.

5. The apparatus of claim 1, wherein the cathodic metal has a higher galvanic potential than the anodic metal.

6. The apparatus of claim 1, wherein the cathodic metal comprises one or more of: palladium, platinum, gold, molybdenum, titanium, iridium, osmium, niobium and rhenium.

7. The apparatus of claim 1, wherein the coating comprises the anodic metal and the cathodic metal that have been vapor-deposited onto the length of filament so that the anodic metal is not encapsulated by the cathodic metal.

8. The apparatus of claim 1, wherein the length of bioabsorbable filament comprises one or more of: polylactic acid (PLA), poly(lactic-co-glycolic acid) (PLGA), polyglycolide (PGA), polyglycoside-co-trimethylene carbonate (PGTMC), poly(caprolactone-co-glycoside), poly(dioxanone) (PDS), and poly(caprolactone) (PCL).

9. The apparatus of claim 1, wherein the length of filament is configured to degrade within the body to form a degradation product including an anion that complexes with ions of the anodic metal and diffuses into the subject's body to form an antimicrobial zone.

10. The apparatus of claim 1, wherein the flexible length of bioabsorbable filament comprises a mesh.

11. The apparatus of claim 1, wherein the flexible length of bioabsorbable filament comprises a bag, envelope, pouch or net configured to hold an implant.

12. The apparatus of claim 1, wherein the flexible length of bioabsorbable filament is configured to at least partially house a pacemaker, defibrillator, neurostimulator, or ophthalmic implant.

13. A bioabsorbable apparatus that galvanically releases antimicrobial ions, the apparatus comprising:
    a plurality of lengths of bioabsorbable filament arranged in a woven structure; and
    a coating on the lengths of filament comprising zinc and silver and a cathodic metal that are all co-deposited onto the lengths of filament, wherein the zinc and silver are at least about 30 percent by volume of the coating and form a non-uniform mixture of the zinc and the cathodic metal and a non-uniform mixture of the silver and the cathodic metal, wherein the coating comprises a plurality of microregions or microdomains of zinc and silver in a matrix of cathodic metal or a plurality of microregions or microdomains of cathodic metal in a matrix of zinc and a matrix of silver, the microregions or microdomains forming a continuous path of interconnected veins of zinc within the matrix of cathodic metal and a continuous path of interconnected veins of silver within the matrix of cathodic metal, wherein the continuous paths extend from an outer surface of the coating to the filament;
    further wherein the zinc and silver are galvanically released as antimicrobial ions when the apparatus is inserted into a subject's body.

14. The apparatus of claim 13, wherein the cathodic metal has a higher galvanic potential than the silver or zinc.

15. The apparatus of claim 13, wherein the cathodic metal comprises one or more of: palladium, platinum, gold, molybdenum, titanium, iridium, osmium, niobium and rhenium.

16. The apparatus of claim 13, wherein the coating comprises the silver and zinc and the cathodic metal that have been vapor-deposited onto the lengths of filament so that the anodic metal is not encapsulated by the cathodic metal.

17. The apparatus of claim 13, wherein the lengths of bioabsorbable filament comprise one or more of: polylactic acid (PLA), poly(lactic-co-glycolic acid) (PLGA), polyglycolide (PGA), polyglycoside-co-trimethylene carbonate (PGTMC), poly(caprolactone-co-glycoside), poly(dioxanone) (PDS), and poly(caprolactone) (PCL).

18. The apparatus of claim 13, wherein the lengths of filament are configured to degrade within the body to form a degradation product including an anion that complexes with ions of the silver and zinc and diffuses into the subject's body to form an antimicrobial zone.

19. The apparatus of claim 13, wherein the woven structure comprises a mesh, a bag, envelope, a pouch or a net configured to at least partially enclose an implant within the subject's body.

20. A bioabsorbable apparatus that galvanically releases antimicrobial ions, the apparatus comprising:
    a plurality of lengths of bioabsorbable filament; and
    a coating on the lengths of filament comprising an anodic metal that is co-deposited with a cathodic metal on the lengths of filament to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming continuous paths of interconnected veins of anodic metal within the matrix of cathodic metal or continuous paths of cathodic metal within the matrix of anodic metal, wherein the continuous paths extend from an outer surface of the coating to the filament;

wherein the lengths of filament are arranged into a flexible structure;

further wherein the anodic metal is galvanically released as antimicrobial ions when the apparatus is inserted into a subject's body.

21. The apparatus of claim 1, wherein the continuous path of interconnected veins are interconnected so that less than 15% of the anodic metal is completely encapsulated within the matrix of cathodic metal, or less than 15% of the cathodic metal is completely encapsulated within the matrix of anodic metal.

22. The apparatus of claim 1, wherein the continuous path of interconnected veins are interconnected so that less than 10% of the anodic metal is completely encapsulated within the matrix of cathodic metal, or less than 10% of the cathodic metal is completely encapsulated within the matrix of anodic metal.

23. The apparatus of claim 13, wherein the continuous path of interconnected veins are interconnected so that less than 15% of the zinc is completely encapsulated within the matrix of cathodic metal and less than 15% of the silver is completely encapsulated within the matrix of cathodic metal, or less than 15% of the cathodic metal is completely encapsulated within the matrix of zinc and less than 15% of the cathodic metal is completely encapsulated within the matrix of silver.

24. The apparatus of claim 13, wherein the continuous path of interconnected veins are interconnected so that less than 10% of the zinc is completely encapsulated within the matrix of cathodic metal and less than 10% of the silver is completely encapsulated within the matrix of cathodic metal, or less than 10% of the cathodic metal is completely encapsulated within the matrix of zinc and less than 10% of the cathodic metal is completely encapsulated within the matrix of silver.

25. The apparatus of claim 20, wherein the continuous path of interconnected veins are interconnected so that less than 15% of the anodic metal is completely encapsulated within the matrix of cathodic metal, or less than 15% of the cathodic metal is completely encapsulated within the matrix of anodic metal.

26. The apparatus of claim 20, wherein the continuous path of interconnected veins are interconnected so that less than 10% of the anodic metal is completely encapsulated within the matrix of cathodic metal, or less than 10% of the cathodic metal is completely encapsulated within the matrix of anodic metal.

* * * * *

UNITED STATES PATENT AND TRADEMARK OFFICE
CERTIFICATE OF CORRECTION

PATENT NO. : 8,927,004 B1
APPLICATION NO. : 14/302352
DATED : January 6, 2015
INVENTOR(S) : Dehnad et al.

It is certified that error appears in the above-identified patent and that said Letters Patent is hereby corrected as shown below:

Column 3, line 33, delete "AgCl+$e$ → Ag+Cl(-) Eo= 0.222 volts" and insert

--AgCl + e → Ag + Cl(-)    Eo= 0.222 volts--.

Column 3, line 63, delete "Ag(+)+$e$(-)→ Ag Eo= 0.800 volt    eq. (1)" and insert --Ag(+) + e(-) → Ag    Eo= 0.800 volt    eq. (1)--.

Column 4, line 2, delete "$O_2$+2$H_2O$+4$e$(-)→4OH(-) Eo=0.401 volt    eq. (2)" and insert --$O_2$ + 2$H_2O$ + 4e(-) → 4 OH(-)$^*$    Eo= 0.401 volt    eq. (2)--.

Column 4, line 3, delete "$O_2$+4H(+)+4$e$(-)→2$H_2O$ Eo=1.229 volt    eq. (3)" and insert --$O_2$ + 4H(+) + 4 e(-) → 2$H_2O$    Eo= 1.229 volt    eq. (3)--.

Column 4, line 21, delete "AgCl+$e$(-)→Ag+Cl(-) Eo=0.222" and insert

--AgCl + e(-) → Ag + Cl(-)    Eo= 0.222--.

Column 4, line 33, delete "*j=D[C(d)-C(c)]/d*    Fick's equation" and insert

--j= D[C(d)- C (c)] / d    Fick's equation--.

Column 4, line 45, delete "i(Ag)=*D*.n.F(C(d))/d*" and insert --i (Ag) = D* .n. F (C(d)) / d--.

Signed and Sealed this
Twenty-third Day of August, 2016

Michelle K. Lee
*Director of the United States Patent and Trademark Office*

CERTIFICATE OF CORRECTION (continued)
U.S. Pat. No. 8,927,004 B1

Column 4, line 60, delete "$i(cl)=\{(10^{\wedge}(-6))*(1)*(96000)*(0.1)/(0.1)\}*(1 \text{ lit}/1000$" and insert --i(cl) = { (10^(-6)) * (1) * (96000) * (0.1) / (0.1) } * (1 lit/1000--.

Column 5, line 4, delete "$i(O2)=\{(0.000324)*(4)*(96000)*(5*10^{\wedge}(-3))/(0.5)\}(1$" and insert --i(O2)= { (0.000324) * (4)*(96000)* (5*10^(-3)) / (0.5)} (1--.

Column 5, line 10, delete "$i$(cathodic)*Area of the cathode=$i$(anodic)*Area of" and insert --i(cathodic) * Area of the cathode = i (anodic) * Area of--.

Column 5, line 29, delete "$\eta = \beta \log [i/io]$" and insert

--$\eta = \beta \log [i/io]$--.